US009624266B2

(12) United States Patent
Singh et al.

(10) Patent No.: US 9,624,266 B2
(45) Date of Patent: Apr. 18, 2017

(54) BRACHIATIN D AND PROCESS FOR PRODUCTION THEREOF

(71) Applicant: COUNCIL OF SCIENTIFIC & INDUSTRIAL RESEARCH, New Delhi (IN)

(72) Inventors: Deepika Singh, Jammu-Tawi (IN); Jai Prakash Sharma, Jammu-Tawi (IN); Sundeep Jaglan, Jammu-Tawi (IN); Abid Hamid Dar, Jammu-Tawi (IN); Anamika Khajuria, Jammu-Tawi (IN); Varun Pratap Singh, Jammu-Tawi (IN); Ram Asrey Vishwakarma, Jammu-Tawi (IN)

(73) Assignee: Council of Scientific & Industrial Research, New Delhi (IN)

( * ) Notice: Subject to any disclaimer, the term of this patent is extended or adjusted under 35 U.S.C. 154(b) by 0 days.

(21) Appl. No.: 14/914,094

(22) PCT Filed: Aug. 29, 2014

(86) PCT No.: PCT/IN2014/000557
§ 371 (c)(1),
(2) Date: Feb. 24, 2016

(87) PCT Pub. No.: WO2015/029069
PCT Pub. Date: Mar. 5, 2015

(65) Prior Publication Data
US 2016/0215017 A1 Jul. 28, 2016

(30) Foreign Application Priority Data

Aug. 30, 2013 (IN) .......................... 2563/DEL/2013

(51) Int. Cl.
C07K 7/06 (2006.01)
A61K 38/00 (2006.01)
C12R 1/885 (2006.01)

(52) U.S. Cl.
CPC .............. *C07K 7/06* (2013.01); *C12R 1/885* (2013.01); *A61K 38/00* (2013.01)

(58) Field of Classification Search
None
See application file for complete search history.

(56) References Cited

U.S. PATENT DOCUMENTS 5,595,756 A * 1/1997 Bally .................. A61K 9/1272
264/4.1

OTHER PUBLICATIONS

Sporn et at, "Chemoprevention of Cancer," Carcinogenesis, vol. 21 (2000), 525-530.*
Gura, "Cancer Models: Systems for Identifying New Drugs Are Often Faulty," Science vol. 278 (1997), 1041-1042.*
Auvin-Guette et al., "Trichogin A IV, an 11-Residue Lipopeptaibol from *Trichoderma longibrachiatum*", *J Am Chem Soc*, 114: 2170-2174, 1992.
Ayers et al., "Peptaibols from two unidentified fungi of the order Hypocreales with cytotoxic, antibiotic, and anthelmintic activities", *Journal of Peptide Science*, 18: 500-510, 2012.
Baker et al., "The value of natural products to future pharmaceutical discovery", *Natural Product Reports*, 24: 1225-1244, 2007.
Cragg et al., "Impact of Natural Products on Developing New Anti-Cancer Agents", *Chem Rev*, 109: 3012-3043, 2009.
Harman et al., "*Trichoderma* Species—Opportunistic, Avirulent Plant Symbionts", *Nature Reviews*, 2: 43-56, 2004.
He et al., "Culicinin D, Antitumor Peptaibol Produced by the Fungus *Culicinomyces clavisporus*, Strain LL-12I252", *J Nat Prod*, 69: 736-741, 2006.
Hermosa et al., "Plant-beneficial effects of *Trichoderma* and of its genes", *Microbiology*, 158: 17-25, 2012.
International Search Report and Written Opinion issued in PCT/IN2014/000557, mailed on Feb. 18, 2015.
Leclerc et al., "Sequences and Antimycoplasmic Properties of Longibrachins LGB II and LBG III, Two Novel 20-Residue Peptaibols from *Trichoderma longibrachiatum*", *J Nat Prod*, 64: 164-170, 2001.
Lorito et al., "Translational Research on *Trichoderma*: From 'Omics to the Field", *Annu Rev Phytopathol*, 48: 19.1-19.23, 2010.
Maddau et al., "Occurrence and characterization of peptaibols from *Trichoderma citrinoviride*, an endophytic fungus of cork oak, using electrospray ionization quadrupole time-of-flight mass spectrometry", *Microbiology*, 155: 3371-3381, 2009.
Mikkola et al., "20-Residue and 11-residue peptaibols from the fungus *Trichoderma longibrachiatum* are synergistic in forming $Na^+/K^+$-permeable channels and adverse action towards mammalian cells", *FEBS Journal*, 179: 4172-4190, 2012.
Mitova et al., "Evolving Trends in the Dereplication of Natural Product Extracts. 2. The Isolation of Chrysaibol, an Antibiotic Peptaibol from a New Zealand Sample of the Mycoparasitic Fungus *Sepedonium chrysoospermum*", *J Nat Prod*, 71: 1600-1603, 2008.
Mohamed-Benkada et al., "New short peptaibols from a marine *Trichoderma* strain", *Rapid Commun Mass Spectrom*, 20: 1176-1180, 2006.
Mukherjee et al., "Secondary metabolism in *Trichoderma*—a genomic perspective", *Microbiology*, 158: 35-45, 2012.
Mukherjee et al., "Two Classes of New Peptaibols Are Synthesized by a Single Non-ribosomal Peptide Synthetase of *Trichoderma virens*", *J Biol Chem*, 286: 4544-4554, 2011.
Neuhof et al., "Intact-cell MALDI-TOF mass spectrometry analysis of peptaibol formation by the genus *Trichodermal Hypocrea*: can molecular phylogeny of species predict peptaibol structures?", *Microbiology*, 153: 3417-3437, 2007.
Rebuffat et al., "Tricholongins BI and BII, 19-residue peptaibols from *Trichoderma longibrachiatum*", *Eur J Biochem*, 201: 661-674, 1991.

(Continued)

*Primary Examiner* — Thomas S Heard
(74) *Attorney, Agent, or Firm* — Norton Rose Fulbright US LLP

(57) ABSTRACT

The present invention relates to a peptaibol having sequence AcAib-Asn-Aib-Leu-Aib-Pro-Aib-Asn-Leu-Pro-Ileuol, isolated from endophytic fungus *Trichoderma longibrachiatum* having accession number MTCC 5721. The peptaibol is named as brachiating D. The present also related to a process for isolating the peptaibol from and use of the peptaibol as a pharmacologically active compound as a strong immunosuppressants and as an anticancer agents.

18 Claims, 9 Drawing Sheets

(56) References Cited

OTHER PUBLICATIONS

Ren et al., "Asperelines A-F, Peptaibols from the Marine-Derived Fungus *Trichoderma asperellum*", *J Nat Prod*, 72: 1036-1044, 2009.

Ruiz et al., "New Trichobrachins, 11-residue peptaibols from a marine strain of *Trichoderma longibrachiatum*", *Peptides*, 28: 1351-1358, 2007.

Summers et al., "Septocylindrins A and B: Peptaibols Produced by the Terrestrial Fungus *Septocylindrium* sp. LL-Z1518", *J Nat Prod*, 70: 391-396, 2007.

* cited by examiner

BRACHIATIN D AND PROCESS FOR PRODUCTION THEREOF

CROSS-REFERENCE TO RELATED APPLICATIONS

This application is a national phase application under 35 U.S.C. §371 of International Application No. PCT/IN2014/000557 filed 29 Aug 2014, which claims priority to Indian Patent Application No. 2563/DEL/2013 filed 30 Aug. 2013. The entire contents of each of the above-referenced disclosures is specifically incorporated herein by reference without disclaimer.

FIELD OF THE INVENTION

The present invention relates to peptaibol having sequence AcAib-Asn-Aib-Leu-Aib-Pro-Aib-Asn-Leu-Pro-Ileuol, said peptaibol is Brachiatin D obtained from an endophytic fungus *Trichoderma longibrachiatum* having MTCC number 5721. The present invention also relates to a process for isolation, identification and purification of brachiatin D. The present invention further relates to use of the isolated peptaibol as potent immunosuppressant and anticancer agent.

BACKGROUND OF THE INVENTION

Natural products of plant endophytes are an untapped promising new resource for drugs having an interesting realm of novel chemistry. Their studies surprisingly reveals that many of the important drugs thought to be produced by plants are probably, the products of their interaction with endophytic microbes residing in tissue between living plant cells. Possessing this incredible adaptability due to their flexible power, they have proved their potential importance, not only in agriculture, industry but, also wonderfully in human health in many therapeutic areas, interestingly unveiling its treasure trove, broadening the landscape of natural product research and discovery. [Annu. Rev. Phytopathol 48: 19.1-19.23 (2010)]. This beautiful mystery of nature as a valuable contributor has taken much of curiosity with deep interest and studies have interestingly unfolded that plants, insects, marine organisms themselves also utilize these natural products to defend themselves against many serious unfavorable biotic and abiotic conditions [Chem Rev 109: 3012-3043 (2009); Nat. Prod. Rep. 24: 1225-1244 (2007)]

*Trichoderma*, a widely applied filamentous biocontrol fungi, found to produce many beneficial effects on plants has passed through several phases in agricultural applications with each new discovery, only adding more, to its usefulness, has been recently redefined as endophytic plant symbionts, which wonderfully extend their stronger potential in disease control as well [US 2012/0096598; Microbiology 158: 17-25 (2012); Microbiology 158: 35-45 (2012); Microbiology 155: 3371-3381 (2009)]. The metabolomics of *Trichoderma* species are incredibly complex, the variety and number of secondary metabolites being produced are astonishingly high. Recent study of genome sequences of *Trichoderma* species has revealed a vast repertoire of genes putatively involved in biosynthesis of secondary metabolites such as Non Ribosomal Peptides, polyketides, terpenoids and pyrones [Nature reviews 2004, 2, 43-56].

Peptaibols, are such unique linear, hydrophobic antibiotic peptides being produced by non-ribosomal peptide synthesases and are proteolytic enzyme-resistant, membrane active peptides, characterized by high content of alpha amino isobutyric acid, isovaline with an N-terminal acyl moiety and C terminus as amino alcohol such as phenylalaninol, valinol or leucinol [J. Nat. Prod. 72: 1036-1044 (2009); J. Biol. Chem. 286, 6: 4544-4554 (2011); Microbiology 153: 3417-3437 (2007)]. Peptide synthetases possess multiple modules that bind, activate and condense each specific amino acid to form the peptide product. The number, organization and order of modules in the peptide synthetase reflect the size of complexity and the sequence of the peptide. It seems that the specificity of each module is variable resulting in the synthesis of micro-heterogeneous mixture. The biological activity of peptaibols has been closely linked to their three dimensional α-helical structures and their potential to form pores in bilayer lipid membranes [J. Nat. Prod. 70: 391-396 (2007); J. Pept. Sci. DOI 10.1002/psc.2425; J. Am. Chem. Soc. 114: 2170-2174(1992); FEM Microbial Lett DOI: 10.1111/febs.12010], antibacterial, antiparasitic [U.S. Pat. No. 6,582,949; U.S. Pat. No. 7,067,112; U.S. Pat. No. 5,432,157], antifungal, occasional antiviral, insecticidal, cyto toxic [J. Nat. Prod. 2008, 71, 1600], antitumor [J.Nat. Prod. 69: 736-741 (2006)], inhibition of mitochondrial ATPase, uncoupling of oxidative phosphorylation, inhibition of platelet aggregation, induction of fungal morphogenesis and neuroleptic effects have also been reported. [J. Nat. Prod. 2001, 64, 164-170].

A Marine strain of *Trichoderma longibraciatum* isolated from mussels (*Mytilus edulis*) from estuary of the Loire river from which micro-hetrogenous mixture of 11 residue peptaibols tricholongins A and C were isolated belonging to peptidic family of Ac-Aib-XXX-XXX-XXX-Aib-Pro-XXX-XXX-Aib-Pro-XXol having cytotoxicity on KB cells [Peptides 28: 1351-1358 (2007)]. 19 residue tricholongins BI and B II [M+Na]$^+$ having 1932 and 1946 Da having antifungal and antibacterial activity collected from walls of a beer cellar. [Eur J. Biochem 201: 661-674 (1991)] and 20 residue longibrachins LGB II and LGB III having antimycoplasmic properties [J. Nat. Prod 64: 164-170 (2001)].

Objective of the Invention

The main object of the present invention is to provide a peptaibol isolated from fungus *Trichoderma longibrachiatum* having immunosuppressant and anticancerous activity.

Another object of the present invention is to culture the fungus *Trichoderma longibrachiatum* both in solid nutrient medium and in liquid fermentation medium to obtain the peptaibol.

Yet another object of the present invention is to isolate the peptaibol from the mycelia of the fungus, and purify.

Still another object of the present invention is to evaluate the activity of isolated peptaibol as an immunosuppressant and an anticancerous agent.

SUMMARY OF THE INVENTION

Accordingly, the present invention provides an, isolated peptaibol having sequence AcAib-Asn-Aib-Leu-Aib-Pro-Aib-Asn-Leu-Pro-Ileuol, wherein AcAib is acetylated α aminoisobutyric acid, Aib is α aminoisobutyric acid, Asn is Asparagine, Leu is Leucine, Pro is Proline and Ileuol is Isoleucinol, represented by structure I.

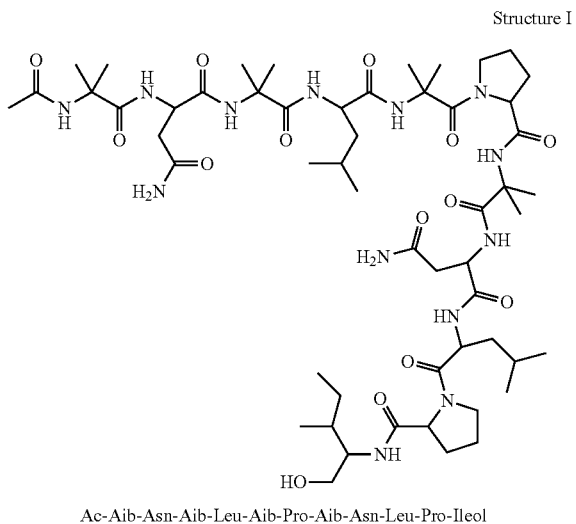 [SMILES: CCC(C)C(CO)NC(=O)C1CCCN1C(=O)C(CC(C)C)NC(=O)C(CC(N)=O)NC(=O)C(C)(C)NC(=O)C1CCCN1C(=O)C(C)(C)NC(=O)C(CC(C)C)NC(=O)C(C)(C)NC(=O)C(CC(N)=O)NC(=O)C(C)(C)NC(C)=O]

Structure I

Ac-Aib-Asn-Aib-Leu-Aib-Pro-Aib-Asn-Leu-Pro-Ileol

In an embodiment of the present invention there is provided a peptaibol, wherein the peptaibol exhibits an immunosuppressant and an anticancer activity.

In another embodiment of the present invention there is provided a peptaibol, wherein the peptaibol exhibits activity against proinflammatory cytokines like TNF α, IL-1β, IL-6, NO and lymphocyte proliferation at a concentration in range of 0.001 μM-10 μM.

In yet another embodiment of the present invention there is provided a peptaibol, wherein the peptaibol is having $IC_{50}$ value in the range of 1 μM-7 μM against cancer cell lines selected from the group consisting of A549 (lung cell line), HOP-62 (lung cell line), THP1 (leukemia cell line), PC-3 (Prostrate cell line), MCF-7 (Breast cell line) and MiaPaCa-2 (Pancreatic cell line).

In still another embodiment of the present invention there is provided a peptaibol, wherein the peptaibol has optimal growth inhibition in the range of 56%-100% in human cancer cell lines at a concentration ranging between 1 μM-50 μM.

Another embodiment of the present invention provides a process for obtaining a peptaibol, the process comprises of the steps:—
a) Isolating an endophytic fungus Trichoderma longibrachiatum;
b) Obtaining a suspension of spores of the fungus by growing the isolated fungus in step (a) in a media;
c) Inoculating a flask containing a broth with the suspension containing $10^5$ to $10^6$ conidia/ml of the fungus and incubating at a temperature in the range of 22 to 28° C. under shaking conditions at 130-200 rpm for 15 to 30 days to obtain a broth of fungal mycelia;
d) Separating the fungal mycelia and conidia from the broth and macerating the fungus mycelia with a solvent for a time period of 45 min to 2 hours to obtain an extract;
e) Evaporating the extract to dryness under reduced pressure in the range of 0.2 to 0.5 bar at a temperature in the range of 25 to 40° C. to obtain a crude mixture; and
f) Purifying the crude mixture obtained in step (e) by chromatography to obtain the peptaibol.

In an embodiment of the present invention there is provided a process for obtaining the peptaibol wherein the media used in step (b) is selected from the group consisting of Malt Extract Broth Base and Potato Dextrose Broth.

In another embodiment of the present invention there is provided a process for obtaining the peptaibol wherein the Trichoderma longibrachiatum is isolated from Boswellia serrata.

In another embodiment of the present invention there is provided a process for obtaining the peptaibol wherein the broth used is selected from the group consisting of Malt Extract Broth Base and Potato Dextrose Broth.

In another embodiment of the present invention there is provided a process for obtaining the peptaibol wherein the solvent used is selected from the group consisting of methanol, dichloromethane and ethyl acetate or a mixture thereof.

In another embodiment of the present invention there is provided a process for obtaining the peptaibol wherein the obtained peptaibol has purity of 99%.

In another embodiment of the present invention there is provided a process for obtaining the peptaibol wherein the yield of peptaibol is in the range of 30 mg to 80 mg from 100 mg to 900 mg of crude mixture.

In another embodiment of the present invention there is provided a process for obtaining the peptaibol wherein the chromatography used for purification is HPLC or reverse phase chromatography.

In yet another embodiment of the present invention there is provided a process for obtaining the peptaibol wherein the reverse phase chromatography is carried out using hydrophobic material RP-8 or RP-18 with a solvent system selected from the group consisting of acetonitrile and trifluoro acetic acid or a mixture thereof.

An embodiment of the present invention provides a novel isolated bacterial strain of Trichoderma longibrachiatum having accession number MTCC 5721.

Another embodiment of the present invention provides a composition comprising the peptaibol having sequence AcAib-Asn-Aib-Leu-Aib-Pro-Aib-Asn-Leu-Pro-Ileuol and a pharmaceutically acceptable carrier or a diluent.

Yet another embodiment of the present invention provides a composition comprising the peptaibol having sequence AcAib-Asn-Aib-Leu-Aib-Pro-Aib-Asn-Leu-Pro-Ileuol for use as an immunosuppressant and an anti-cancer agent.

BRIEF DESCRIPTION OF THE DRAWINGS

FIG. 3 (b) provides MS/MS studies showing fragmentation pattern of mass having m/z 1199 Da showing presence of diagnostic characteristic fragment ions of peptaibols.

FIG. 3 (c) provides MS/MS studies showing fragmentation pattern of mass having m/z 1959 Da showing presence of diagnostic characteristic fragment ions of peptaibols.

FIG. 5 (b) provides the Mass spectra showing separation of long chain of peptaibols from the mixture of peptaibols.

FIG. 8 (b) provides the MS/MS studies of purified Brachiatin D having mass with m/z 1199 Da.

FIG. 9 (b) shows the effect of purified Brachiatin D on the level of IL-6.

FIG. 9 (c) shows the effect of purified Brachiatin D on the level of IL-1 β.

FIG. 9 (d) shows the effect of purified Brachiatin D on the level of NO.

ABBREVIATIONS USED

Figure 1:
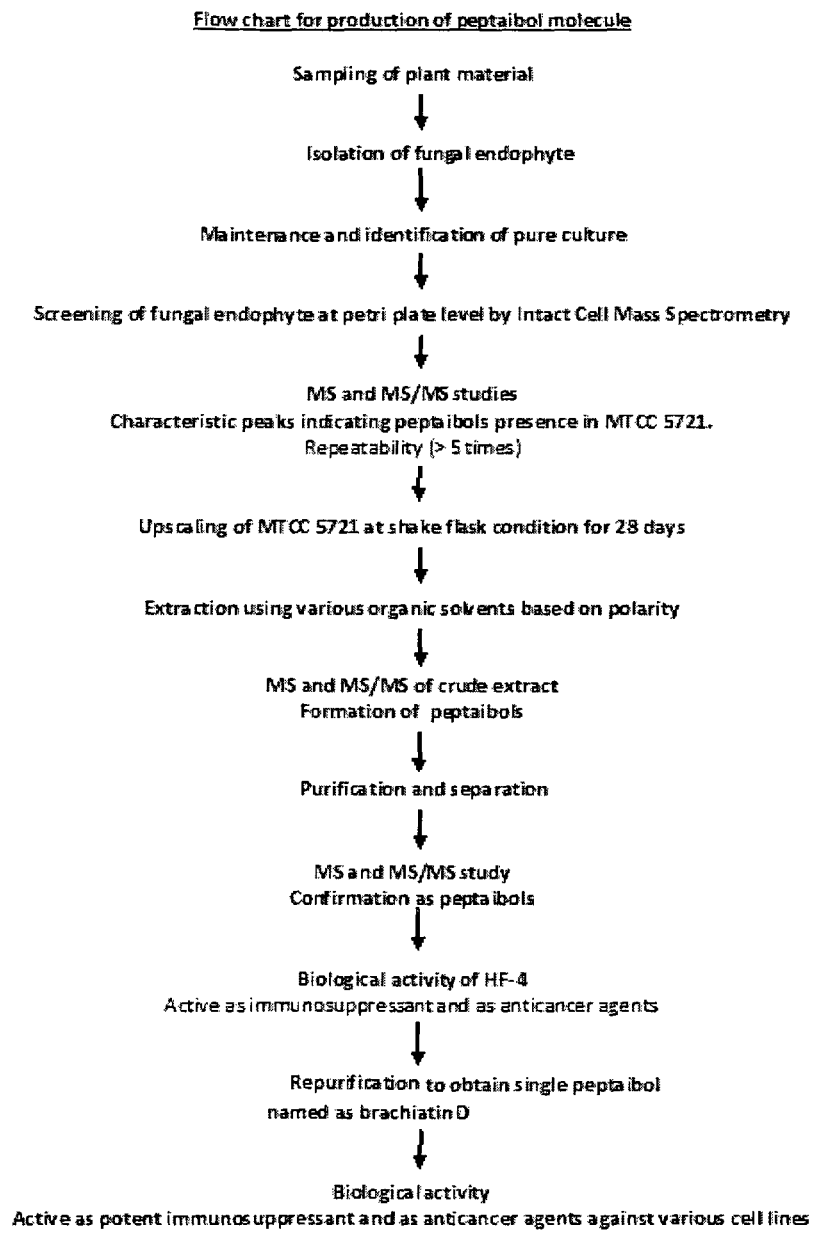
FIG. 1 represents the flow chart for production of the peptaibol.

MALDI TOF/TOF: Matrix-Assisted Laser Desorption/Ionisation Time Of Flight/Time Of Flight
HF-4: HPLC purified Fraction 4
Con A: Concanavalin A
LPS: Lipopolysaccharide
BMS: Betamethasone

DETAILED DESCRIPTION OF THE INVENTION

The object according to the present invention is achieved by identifying one endophytic fungus out of 7 (BS-1 to BS-7) and isolating endophytic fungus screened for having possible active peptaibol formation. One endophytic fungus, BS-4 identified as *Trichoderma longibrachiatum* having accession no. MTCC 5721, is cultured both in solid nutrient medium and liquid shake flask fermentation conditions, until the novel peptaibol named as brachiatin, accumulate in the cell mass. The brachiatin so obtained is isolated from the cell mass, followed by its separation and purification into individual active peptaibol.

The novel peptaibol named as brachiatin D isolated for the first time from an endophytic fungus *Trichoderma longibrachiatum* having accession number MTCC 5721, has a novel sequence Ac-Aib-Asn-Aib-Leu-Aib-Pro-Aib-Asn-Leu-Pro-Ileol. This peptaibol belongs to SF4 peptidic family with acetylated N terminus with Aib and having Aib-Pro labile bond at $5^{th}$-$6^{th}$ and $9^{th}$-$10^{th}$ positions. Brachiatin D contains novel sequence with Aib and Asn at position $7^{th}$ and $8^{th}$ respectively and shows potent activity against proinflammatory cytokines at very low concentrations can be employed in particular as an immunosuppressants and as an anticancer agents against varied cancer cell lines.

The sequence of the isolated peptaibol, Brachiatin D is as follows:—
Ac-Aib-Asn-Aib-Leu-Aib-Pro-Aib-Asn-Leu-Pro-Ileuol

| AcAib | Acetylated α aminoisobutyric acid |
| --- | --- |
| Aib | α-amino isobutyric acid |
| Asn | Asparagine |
| Leu | Leucine |
| Pro | Proline |
| Ileuol | Isoleucinol |

The peptaibol, Brachiatin D has the following structure I

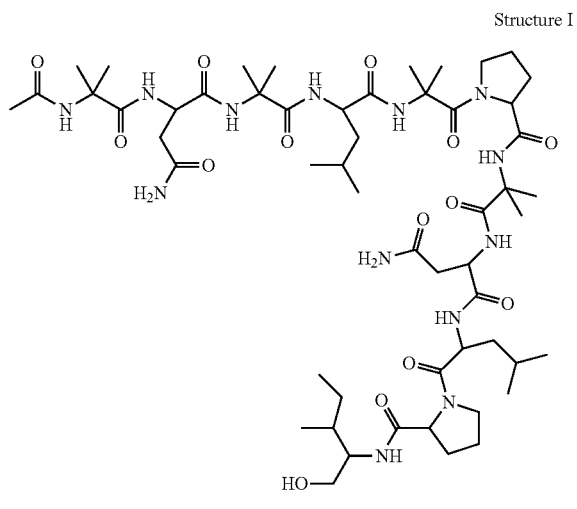

Structure I

Ac-Aib-Asn-Aib-Leu-Aib-Pro-Aib-Asn-Leu-Pro-Ileol

Medium used and their Composition

The mediums that are used in the present invention are given below:

| Chemical | Amount |
| --- | --- |
| Potato Dextrose Agar | |
| Infusion from potatoes | 200 gL$^{-1}$ |
| Dextrose | 20.0 gL$^{-1}$ |
| Agar | 15.0 gL$^{-1}$ |
| pH | 5.6 ± 0.2, |
| Malt Extract Agar Base | |
| Malt extract | 30.0 gL$^{-1}$ |
| Mycological peptone | 5.0 gL$^{-1}$ |
| Agar | 15.0 gL$^{-1}$ |
| pH | 5.4 ± 0.2 |
| Yeast Malt Agar | |
| Yeast extract | 4.0 gL$^{-1}$ |
| Malt extract | 10.0 gL$^{-1}$ |
| Glucose | 4.0 gL$^{-1}$ |
| pH | 5.5 ± 0.2 |

Malt extract broth base (MEB) or Potato Dextrose Broth (PDB) are used to scale up the production of peptaibol in the shake flask batch fermentation. All the media used were procured from HiMedia Laboratories Pvt. Limited, India.

Screening of Fungal Endophyte at Petri Plate Level by Intact Cell Mass Spectrometry Screening for possible peptaibol formation in all isolated endophytic fungus is carried out at early stages by Intact Cell Mass Spectrometry by MALDI TOF/TOF mass spectrometer. 1 mg-10 mg of sporulating fungal culture, was scraped from the solid nutrient agar surface on agar petri plates carefully by sterilized spatula avoiding any media interference and suspended in water immiscible organic solvents like dichloromethane, ethyl acetate or organic solvents like methanol, acetonitrile or preferably a mixture of dichloromethane: methanol: water (3:1:1) or acetonitrile: methanol: water (1:1:1 by volume) in a volume in the range of 10 μl to 100 μl preferably with 20 μl, mixed well by vortexing and centrifuging at 3,500 to 10000 rpm for 5-25 min, preferably at 5000 rpm for 10 min. The synthesis of peptaibol according to the present invention takes place particularly in the sporulation stage of the culture of

*Trichoderma longibrachiatum* having accession number MTCC 5721 having olive green growth, and at mycelium stage, the synthesis of peptaibol occurs in both solid state nutrient media and liquid shake flask fermentation.

MS and MS/MS Studies

Maldi-TOF mass spectra was obtained on Applied Biosystems 4800 MALDI TOF/TOF analyser (AB Sciex, Foster city, USA), having variable ion path length to accommodate both MS linear and high performance two stage reflector mode along with high energy, collision induced (CID) cell in MS/MS mode equipped with Nd:YAG 200 Hz laser. 10 µl to 20 µl of supernatant solution obtained after centrifuging the sporulating fungal culture after suspending it in solvents described above at 3,500 to 10000 rpm for 5-25 min, preferably at 5000 rpm for 10 min, is then premixed with 10 µl to 100 µl solution of matrix solution like 5 mg of α-Hydroxy Cinnamic acid (CHCA) dissolved in 1 ml of 70:30 ACN:$H_2O$, 5 mg of CHCA dissolved in 1 ml of 50:50 ACN:$H_2O$, 5 mg of CHCA dissolved in 1 ml of 70:30 ACN:$H_2O$ with 0.1% TFA, 5 mg of CHCA dissolved in 1 ml of 70:30 ACN:$H_2O$ with 1% TFA, 5 mg of CHCA:DHB dissolved in 1 ml of 50:50 ACN:$H_2O$ with 0.1% TFA, 5 mg of CHCA:DHB dissolved in 1 ml of 70:30 ACN:$H_2O$ with 0.1% TFA, 5 mg of DHB dissolved in 1 ml of 70:30 ACN:$H_2O$, 5 mg of DHB dissolved in 1 ml of 50:50 ACN:$H_2O$, 5 mg of DHB dissolved in 1 ml of 70:30 ACN:$H_2O$ with 0.1% TFA, 5 mg of DHB dissolved in 1 ml of 50:50 ACN:$H_2O$ with 0.1% TFA, preferably in 5 mg of CHCA dissolved in 1 ml of 70:30 ACN:H2O with 0.1% TFA, homogenized and mixed properly by vortexing for another 20 min in an eppendorf tube and 0.3 to 1 µl of the obtained mixture was directly spotted onto target wells of 96 or 364 well sample plate using premixed two layer volume technique or dried droplet volume technique and allowed to air dry prior to analysis.

Upscaling of MTCC 5721 at Shake Flask Condition

The microorganism *Trichoderma longibrachiatum* having accession number MTCC 5721 is cultured aerobically with shaking or stirring in shaker flasks or fermenters, with introduction of air or oxygen. Culturing is advantageously carried out in several stages, i.e. one or more pre-cultures are first prepared in liquid culture medium, which are then inoculated into the actual production medium, the main culture, for example, in the volume ratio 1:10. Culturing is carried out at a temperature range of 18-35° C., preferably at a range of 20 to 30° C., more particularly at 22 to 28° C. The pH is in the range of 5 to 8, preferably 5.3 to 7.0 In general, the microorganism is cultured under these conditions over a period of 168 to 700 hrs, preferably 672 hrs.

Fermentation conditions described above apply to *Trichoderma longibrachiatum* having accession no. MTCC 5721 and can be employed for fermentation on a laboratory scale (culture volumes between ml and litres). The microorganism is cultured aerobically with shaking or stirring in shake flasks or fermenters. The course of fermentation is monitored by means of measuring the pH of the culture or the mycelium volume, by Intact Cell Mass Spectrometry by MALDI TOF/TOF mass spectrometer or by other important chromatographic methods such as thin layer chromatography or high pressure liquid chromatography or by testing the biological activity. The peptaibol according to the present invention are obtained both in cell mass and in the culture filtrate, but the large amount is obtained from the cell mass. The steps followed for the isolation of peptaibol of the present invention can be summarized as following:—

Screening of the endophytic fungus that synthesises peptaibol is carried out according to the following steps:

1. Separation of the mycelium or cell mass after fermentation;
2. Extraction of the mycelium or the cell mass with an organic solvent;
3. Extraction of the peptaibol from the culture filtrate using solid phases or water-immiscible organic solvents;
4. Analysis of the peptaibol by means of Intact Cell Mass Spectrometry (ICMS) by MALDI TOF/TOF mass spectrometer, TLC, HPLC or by testing the biological activity.

Extraction Using Various Organic Solvents Based on Polarity

The isolation or purification of the peptaibol as described in the present invention is carried out from the total growth of the fungus, taking into account the chemical, physical and biological properties of the natural substances.

To carry out the isolation of peptaibol, the mycelium or the cell mass is first separated from the culture medium by the customary processes and the peptaibol are then extracted from the mycelium or the cell mass using water miscible organic solvents like methanol, ethanol, propyl alcohol and acetonitrile. The culture filtrate is optionally combined with the concentrate of the cell mass extract and extracted with a suitable, water immiscible organic solvent such as dichloromethane, ethyl acetate or butyl acetate. The culture broth and the mycelium are extracted at the end of the fermentation one to five times, preferably three times. Ultrasound is used to induce a mechanical stress on the cells through the production of cavitations in the sample. The cellular breakdown increases the solubilisation of the metabolites in the solvent and improves extraction yield. The efficiency of the extraction depends on the instrument frequency, and length and temperature of sonication. The organic solvent phase contains the peptaibol; they are optionally concentrated in vacuo and further purified as described below. For the defatting of the product of the value, it is also possible to dilute the concentrate with a non-polar solvent in which the peptaibol are soluble to a very small extent, such as, for example with hexane, petroleum ether or diethyl ether. The peptaibol precipitates in this process and the lipophilic impurities remain dissolved and are removed by customary solid/liquid phase separations. The precipitate, which contains all the peptaibol, is dissolved in 1/30 of the original volume of water/methanol. The precipitate dissolves completely into solution during this course and the solution is lyophilized. The lyophilizate, subsequently called the crude product, contains 5 to 80% of peptaibol and is employed for further isolation. The mixture preferably consists of detectable peptaibol. In the culture medium, *Trichoderma longibrachiatum* having accession no. MTCC 5721 synthesises a peptaibol named as brachiatin D. The formation of peptaibols, particularly brachiatin D is largely favoured at sporulation stage and giving stress at initial stages of growth in presence of light.

MS and MS/MS of Crude Extract

MALDI-TOF mass spectra was obtained on Applied Biosystems 4800 MALDI TOF/TOF analyser (AB Sciex, Foster city, USA), having variable ion path length to accommodate both MS linear and high performance two stage reflector mode along with high energy, collision induced (CID) cell in MS/MS mode equipped with Nd:YAG 200 Hz laser. Calibration was conducted through mass standard kit for calibration of AB ACIEX TOF/TOF instruments with protein mixture of des-Arg1-Bradykinin (2-9 clip 904.4681), Angiotensin I human (1296.6853), Glu-fibrinopeptide B (1570.6774), ACTH (1-17 clip) (2,093.0867), ACTH (18-39 clip) (2465.1989). Mass accuracy specification was kept at ±0.05 Da. Sample was mixed in the ratio of 1:1 with matrix 70:30 ACN:$H_2O$ (v/v). The instrument was operated in positive ion reflectron mode extracting ions at 10 different regions of same sample spot and each was the result of the accumulation of at least 1000 laser shots having 8-12 subspectra with 100 shots per subspectra, in mass range from 500 to 2500 m/z. Bin size was kept 0.5 ns and band width was kept 500 MHz. The S/N ratio was set from 50-100 to reduce ions arising from matrix and their clusters, small peptides and other unknown contaminants.

Purification Through HPLC

Separation and purification of the peptaibol is carried out on the basis of their differing polarity with the aid of reverse phase chromatography, for example on Agilent 1200 series, on further hydrophobic materials such as for example RP-8 or RP-18 phases. The chromatography is carried out with mixtures of aqueous solutions with alcohols or other water miscible organic solvents. The organic solvents used are preferably acetonitrile or methanol or a mixture thereof. Buffered or acidified aqueous solutions such as ammonium acetate or phosphate buffer in the concentration of 0.1 mM to 0.5 mM, and formic acid, trifluoroacetic acid or all customary acids in a concentration in the range of 0.001 to 1% are in HPLC. The preferred concentration is 0.1%. Chromatography is carried out with gradient or an isocratic grade with a flow rate of 1-2 ml/min observed at 214, 220 and 254 nm.

MS and MS/MS

Mass spectra was obtained on Applied Biosystems 4800 MALDI-TOF/TOF analyser (AB Sciex, Foster city, USA), having variable ion path length to accommodate both MS linear and high performance two stage reflector mode along with high energy, collision induced (CID) cell in MS/MS mode equipped with Nd:YAG 200 Hz laser. The extraction voltage was 20 kV and gated matrix suppression was applied to prevent the saturation of detector by matrix ions. Sample was mixed in the ratio of 1:1 or 1:2 with matrix 70:30 ACN:$H_2O$ with 0.1 to 1% TFA (v/v). The instrument was operated in positive ion reflectron mode extracting ions at 8-15 different regions of same sample spot and each was the result of the accumulation of at least 1000 laser shots having 12 subspectra with 100 shots per subspectra, in mass range from 500 to 2500 m/z. Bin size was kept 0.5 ns and band width was kept 500 MHz. The S/N ratio was set from 50 to reduce ions arising from matrix and their clusters, small peptides and other unknown contaminants.

Biological Activity of the Peptaibol

For Lymphocyte Proliferation Assay, the organic crude extract and then the purified peptaibol was taken for lymphocyte proliferation assay to check their activity by the following procedure. The mice spleen was collected from a live animal after sacrificing it under aseptic conditions in HBSS. The spleen was then minced using a pair of scissors and passed through a fine steel mesh to obtain a homogeneous cell suspension and the erythrocytes were lysed with ammonium chloride (0.8%, w/v). After centrifugation (380×g at 4° C. for 10 min), the pelleted cells were washed three times with PBS and resuspended in complete medium [RPMI 1640 supplemented with 12 mM HEPES (pH 7.1), 0.05 mM 2-mercaptoethanol, 100 IU/mL penicillin, 100 pg/mL streptomycin and 10% FCS]. The cell number was counted with a haemocytometer by the trypan blue dye exclusion technique. Cell viability exceeded 95%.

Splenocytes ($2\times10^6$ cells) were then seeded into a 96-well flat-bottom microtiter plate in 100 µl complete medium. Thereafter, variable doses of the test material along with LPS (1 µg/ml) to stimulate B cell proliferation were added giving a final volume of 200 µl. Test materials used in this assay were variable doses of the purified peptaibol (0.001, 0.01 and 0.1 µM). The plates were then incubated at 37° C. in 95% humidity at 5% $CO_2$ in a $CO_2$ incubator for 72 hrs. After 72 h, 50 µl of MIT solution (5 mg/ml) was added to each well and the plates were incubated for 4 h. Thereafter, plates were centrifuged (1400×g, 5 min) and the untransformed MTT was removed. 200 µl of DMSO (192 µl DMSO with 8 µl IN HCl) was added to each well, and the absorbance was determined in an ELISA reader at 570 nm after 15 min.

For Cytotoxic assay, the MTT assay is useful for measuring the effect of a wide range of compounds on the in vitro growth of either normal or cancer cell lines. The assay was set up in a 96-well, flat-bottomed polystyrene microtiter plate. 3-5000 cancer cells were suspended per well in appropriate growth medium, and the cells were added in duplicate wells (triplicates were preferred). It was preferable to add the cells to the required number of wells in the plate prior to adding the peptaibol. After the cells were added to the plate, it was placed on an incubator for overnight incubation. After overnight incubation, the peptaibol was added at defined concentrations of 10, 20 and 50 µM to each set of duplicate wells and incubated for 48 hrs in $CO_2$ incubator. The peptaibol was dissolved in dimethyl sulfoxide (DMSO) for the final addition. After 48 hr incubation, the MTT stock solution (2.5 µg/ml) was diluted with an equal volume of tissue culture medium and 20 µl of this solution was added directly to each well with a multichannel pipette. The plates were returned to the incubator for a period of at least 4 h. After 4 hr incubation, the plates were centrifuged at 1000 rpm for 10 min at ambient temperature, followed by inversion of the plates and blotting of excess medium. 150 µl of working DMSO was added to solubilize the MTT formazan product. A standard micro plate reader with adjustable wavelength across the visible spectrum was used. The OD values at 570 nm obtained for each set of triplicates corresponding to a specific concentration of a peptaibol was then transferred into a spreadsheet program. The results obtained is as provided in below table 1.

TABLE 1

| | | | | | Tissue Type | | | |
| | | | | | | Normal | | |
| | | | Lung | Liver | Breast | monkey | Ovary | Leukemia |
| | | | | | | Cell Line Type | | |
| S. No. | Sample | Conc. (µM) | A-549 | HEP-2 | MCF-7 | CV-1 | OVCAR-5 | THP-1 |
| | | | | | % growth inhibition | | | |
| 1 | 11 mer (Peptaibol) (1199Da) | 50 | 79 | 87 | 99 | 2 | 93 | 99 |

TABLE 1-continued

|  |  |  | Tissue Type | | | | | |
|---|---|---|---|---|---|---|---|---|
|  |  |  | Lung | Liver | Breast | Normal monkey Cell Line Type | Ovary | Leukemia |
| S. No. | Sample | Conc. (µM) | A-549 | HEP-2 | MCF-7 | CV-1 | OVCAR-5 | THP-1 |
|  |  |  |  |  | % growth inhibition | | | |
| 2 | 5-Fluorouracil | 20 | 75 | — | — | — | — | 83 |
| 3 | Adriyamycin | 1 | — | — | 73 | — | — | — |

Repurification Through HPLC

Further purification of peptaibol of the present invention is carried out on the basis of their differing polarity with the aid of reverse phase chromatography on Agilent 1200 series, on further hydrophobic materials such as RP-8 or RP-18 phases. The chromatography is carried out with mixtures of aqueous solutions with alcohols or other water miscible organic solvents. The organic solvents used are preferably acetonitrile, or acetonitrile with 0.1% TFA (Trifluoro acetic acid) and methanol. Chromatography is carried out with gradient, preferably a linear gradient from 40-85% propanol or acetonitrile with or without 0.1 to 1% TFA or on isocratic mode with a flow rate of 1-2 ml/min observed at 220 nm and 254 nm 30-50 mg of peptaibol is obtained at RT of 30 minutes.

Biological Activity of the Peptaibol

For the estimation of pro-inflammatory cytokines (TNF-α, IL-1β and IL-6) in spleen cell culture supernatant, the splenocytes ($2 \times 10^6$ cells) were seeded into a 96-well flat-bottom microtiter plate in 100 µl complete medium [RPMI 1640 supplemented with 12 mM HEPES (pH 7.1), 0.05 mM 2-mercaptoethanol, 100 IU/mL penicillin, 100 µg/mL streptomycin and 10% FCS]. Thereafter, variable does of purified peptaibol (brachiatin D) (0.001, 0.01 and 0.1 µM) were added giving a final volume of 200 µl. After subsequent stimulation with 1 µg/ml LPS for 24 h, the supernatants were harvested. The concentrations of TNF-α, IL-1β and IL-6 in culture supernatants were measured using mouse TNF-α, IL-1β and IL-6 ELISA kits (R&D Systems, USA), as per the instructions of the manufacturer The isolated peptaibol of the present invention are stable at a pH in the range of 5 to 8, in particular from 5 to 7, and therefore can be incorporated into customary pharmaceutical preparations.

Because of their valuable pharmacological properties, the peptaibol of the present invention are suitable for use as pharmaceuticals in human and/or veterinary medicine. The peptaibol of the present invention possess pharmacological activity, in particular as an immunosuppressant and as an anticancer agent against varied cell lines.

EXAMPLES

The following examples are given by way of illustration and therefore, should not be construed to limit the scope of the present invention.

Example 1

Sampling, Isolation and Maintenance of *Trichoderma longibrachiatum* having MTCC No. 5721
Sampling of Plant Material
Stem bark of *Boswellia serrata* (Family: Burseraceae) were collected in January 2010 from healthy and symptomless mature tree of approximately 15 years of age, located in the campus of Indian Institute of Integrative Medicine, Jammu (32.73° N 74.87° E), India. Fresh samples were taken to laboratory, stored in polybags at 4° C. and processed within 4 hours of collection.

Isolation of Fungal Endophyte

Stem bark samples of *Boswellia serrata* were first washed with tap water and processed for isolation of the endophytic fungi. The upper dead tissue of the bark was removed by sharp sterilized knife and sample was further washed with autoclaved distilled water. The samples were surface sterilized by consecutive treatment with 70% ethanol for 1 min, 1% sodium hypochlorite (NaOCl) for 5 min, and 70% ethanol for 30 sec. After each treatment, sample was rinsed with sterile distilled water. The surface sterilized sample was cut into 6 mm×6 mm pieces by using sterilized surgical blades and placed on petridishes containing Agar (2% agar) medium having pH 5.5, supplemented with 200 µg/ml streptomycin sulphate (HiMedia Laboratories, India). The petridishes were incubated at 28° C. for 3-15 days until the mycelium or colony appeared from the inoculated sample. Hyphal tips of fungi growing from the pieces of plant were placed on potato dextrose agar and fungal colonies were allowed to grow.

Maintenance and Identification of Pure Culture

DNA extraction method as described by Liu et al. (2000), was followed to obtain pure genomic DNA of fungal endophyte. PCR amplification of ITS1-5.8S rDNA-ITS2 regions was performed by using universal primers ITS1, Forward primer sequence: 5'-TCCGTAGGTGAACCTGCGG-3' or ITS5, Forward primer sequence: 5'-GGAAG-TAAAAGTCGTAACAAGG-3'; and ITS4, Reverse Primer sequence: 5'-TCCTCCGCTTATTGATATGC-3' (IDT, Lowa USA) (White et al. 1990) in Mastercycler® proS Thermal Cycler of Eppendorf. PCR amplification was performed in a 50 µreaction volume with 25 µl of PCR Master Mix (Promega Corp., Madison, Wis.), 2.50 µl of 10 µM each primer, 3 µl of fungal genomic DNA (100 ng), and 17 µl Molecular biology grade water. The thermal cycling program was as follows: initial denaturation 95° C. for 5 min; 35 cycles of 30 s at 94° C., 45 s at 56° C., and 60 s at 72° C.; and a final extension of 10 min at 72° C. The PCR product was cleaned with UltraClean™ PCR Clean-up DNA purification kit (MO BIO Carlsbad, Calif.) according to manufacturer protocol. Sequencing of purified amplified PCR product was done on multi capillary DNA sequencer, ABI PRISM® 3130xl genetic analyzer (Applied Biosystems, USA) following the manufacturer's instructions. To identify the endophytic fungi, the sequences obtained were used as query sequence for similarity search by using BLAST algorithm against the database maintained at NCBI (http://www.ncbi.nlm.nih.gov). The ITS1-5.8S rDNA-ITS2 sequence of isolate was aligned with the most similar reference sequences of the taxa by using the CLUSTAL X program (Thompson et al., 1997).

A phylogenetic tree was constructed by using software MEGA4 (Tamura et al., 2007) and subsequently analyzed for evolutionary distances by the neighbour joining method. The robustness of clades was estimated by bootstrap analysis with 1000 replications. The contiguous rDNA sequences of the representative isolate was submitted to GenBank database using SEQUIN program with Accession no. JQ665239. The fungal isolate was designated as *Trichoderma longibrachiatum* on the basis of above said analysis of sequences of the amplified region ITS1-5.8S rDNA-ITS2 (FIG. 1).

The isolate was also deposited on Oct. 16, 2012 in Microbial Type Culture Collection and Gene Bank(MTCC) at Institute of Microbial Technology, Sector 39-A, Chandigarh, India, 160 036 under Budapest Treaty on the International recognition of the deposit of microorganisms. The accession number allotted to the fungal isolate EF-BS-4, *Trichoderma longibrachiatum* was MTCC 5721. The deposition certificate, from BP/4 for the acceptance of the culture at MTCC and form BP/9-viability statement of the culture are the part of the specification. Pure culture of endophytic fungi *Trichoderma longibrachiatum* having accession no. MTCC 5721 was obtained and lyophilized culture was maintained at 4° C. for long term preservation. The stock cultures were stored at 4° C. on YMA (Yeast Malt Agar) slants and revived after every 15 days to maintain the stability of culture.

Morphological and Microscopic Analysis of *Trichoderma longibrachiatum* Having Accession No. MTCC 5721

Figure 2:
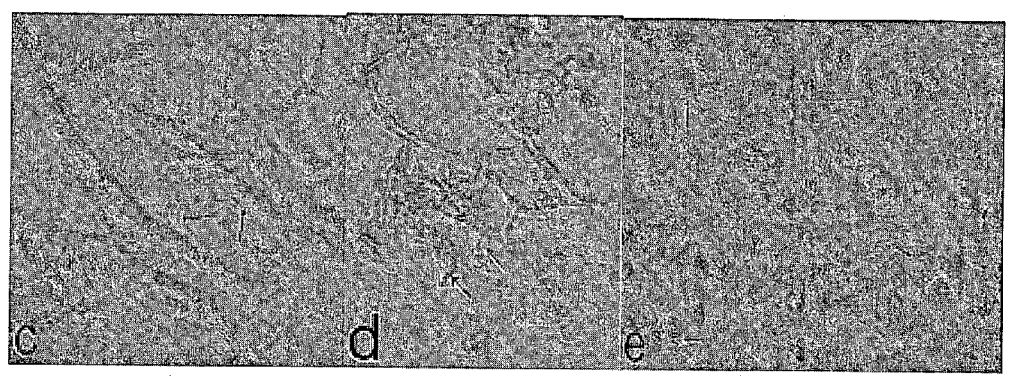
FIG. 2 provides the morphological examination of MTCC 5721. Light micrograph of hyaline sparingly branched hyphae (c), solitary cylindrical phialides (d), smooth-walled, hyaline chlamydospores (e).

Fungal culture of age 3 and 7 days was stained with lactophenol cotton blue and mounted in polyvinyl lactic acid glycerol (PVLG) by incubation at 65° C. for 2-3 days and observed under light microscope. The fungal isolate possesses hyaline sparingly branched hyphae, solitary cylindrical phialides, and smooth-walled hyaline chlamydospores, characteristic of *Trichoderma longibrachiatum* (FIG. 2). FIG. 2 provides the morphological examination of MTCC 5721. Light micrograph of hyaline sparingly branched hyphae (c), solitary cylindrical phialides (d), smooth-walled, hyaline chlamydospores (e). The endophytic fungus having accession no. MTCC 5721 observed to give olive green growth on PDA media, imparted after sporulation.

Cultivation and Fermentation of *Trichoderma longibrachiatum* Having Accession No. MTCC 5721

Batch fermentations were performed in Erlenmeyer flasks (1 L) on Malt extract broth base (Malt extract 17.0 gL$^{-1}$, Mycological peptone 3.0 gL$^{-1}$) pH 5.4±0.2 and Potato dextrose broth (Infusion from potatoes 200 g L$^{-1}$, Dextrose 20.0 g L$^{-1}$) pH 5.1±0.2. Each flask containing 300 ml broth were inoculated with conidial suspension (10$^6$ spores ml$^{-1}$) of fungus and incubated at 28° C. in dark with shaking condition (200 rpm) for 28 days.

Example 2

Sample Preparation and Screening by Intact Cell Mass Spectroscopy (ICMS)

1 mg-5 mg of fungal mycelia obtained according to Example 1 was scraped carefully from agar petri plates avoiding any media interference and then suspended in Acetonitrile/methanol/water (1:1:1 by volume). The suspension was mixed well by vortexing and centrifuged at 5000 rpm for 15 min., 10 µl of supernatant solution was then premixed with 10 µl of matrix solution, (5 mg of CHCA dissolved in 1 ml of 70:30 ACN: Water), homogenized and again mixed properly by vortexing for another 20 min in an eppendorf tube. 1 µl of this mixture was directly spotted onto target wells of 364 well sample plate using premixed two layer volume technique and allowed to air dry prior to analysis. Mass spectra was obtained on Applied Biosystems 4800 MALDI TOF/TOF analyser (AB Sciex, Foster city, USA), having variable ion path length to accommodate both MS linear and high performance two stage reflector mode along with high energy, collision induced (CID) cell in MS/MS mode equipped with Nd:YAG 200 Hz laser. Sample was mixed in the ratio of 1:1 with matrix 70:30 ACN:H$_2$O (v/v). The instrument was operated in positive ion reflectron mode extracting ions at 10 different regions of same sample spot and each was the result of the accumulation of at least 1000 laser shots having 10 subspectra with 100 shots per subspectra, in mass range from 500 to 2500 m/z. Bin size was kept 0.5 ns. The S/N ratio was set at 100 to reduce ions arising from matrix and their clusters, small peptides and other unknown contaminants.

Figure 3A:
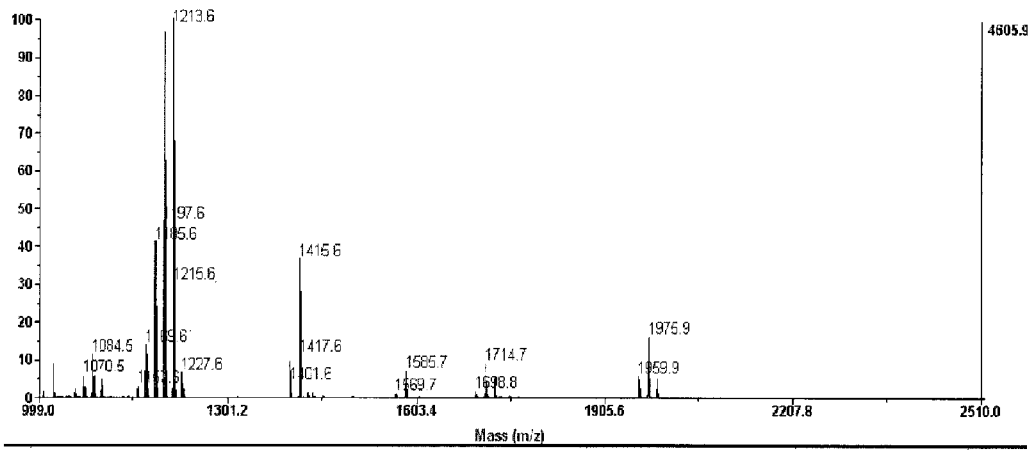
FIG. 3 (a) provides the Initial Screening of endophytic fungus Trichoderma longibrachiatum (MTCC 5721) through Intact Cell Mass Spectrometry showing possible presence of chains of peptaibols.
Figure 3:
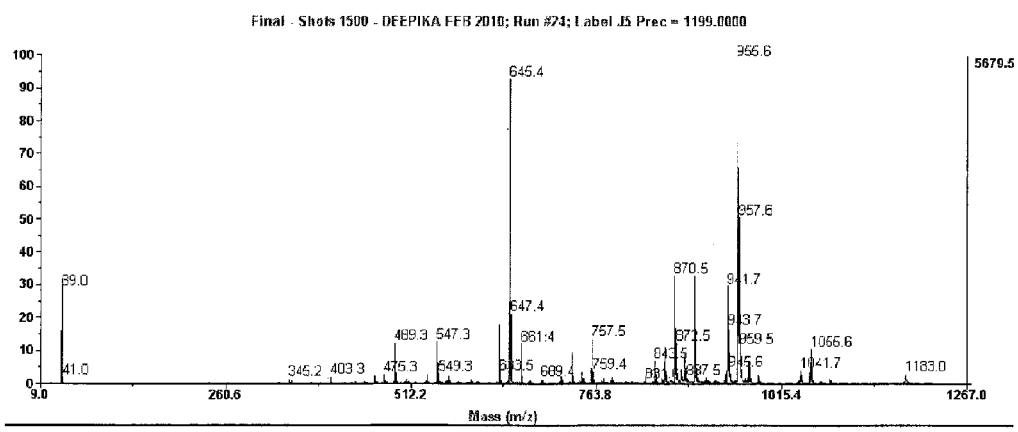
Figure 3:
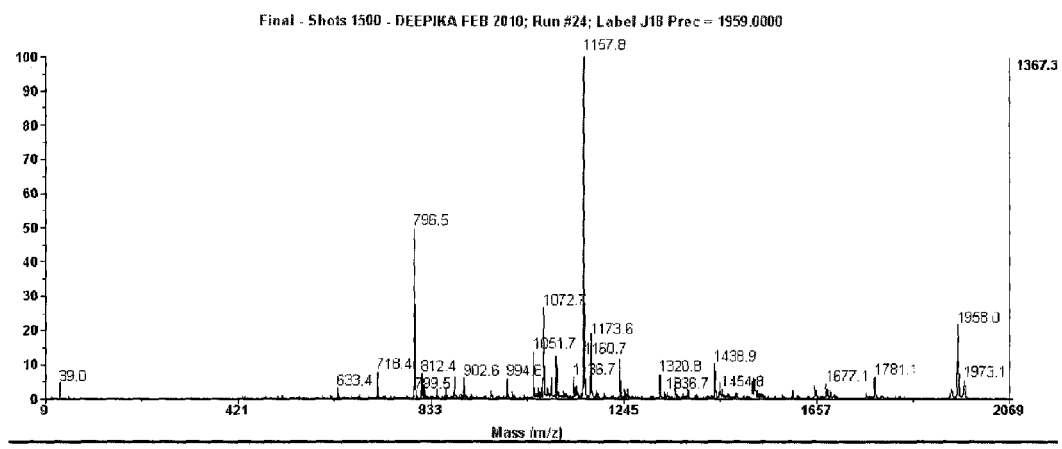

Isolation of Peptide Mixture from the Standard Static Condition of *T. longibrachiatum* Having Accession No. MTCC 5721 and Confirmation of Peptaibol Formation by Diagnostic Fragment Ions Through MS/MS Studies by MALDI TOF/TOF Initial screening was done by ICMS for seven endophytic fungus BS-1 to BS-7 through MALDI TOF/TOF mass spectrometer in the mass range from 1000-2500 Da. Only one endophytic strain BS-4, identified as *Trichoderma longibrachiatum* having accession no. MTCC 5721 was found to contain peptide like molecules with following monoisotopic masses as shown in FIG. 3(a). FIG. 3 (a) provides the Initial Screening of endophytic fungus *Trichoderma longibrachiatum* (MTCC 5721) through Intact Cell Mass Spectrometry showing possible presence of chains of peptaibols. FIG. 3 (b) provides MS/MS studies showing fragmentation pattern of mass having m/z 1199 Da showing presence of diagnostic characteristic fragment ions of peptaibols. FIG. 3 (c) provides MS/MS studies showing fragmentation pattern of mass having m/z 1959 Da showing presence of diagnostic characteristic fragment ions of peptaibols. Peptide mixture obtained with following m/z with masses 1169 Da (M+Na)$^+$, 1183 Da (M+Na)$^+$, 1197 Da (M+Na)$^+$, 1199 Da (M+Na)$^+$, 1213 Da (M+Na)+, 1415 Da (M+Na)$^+$, 1585 Da (M+Na)$^+$, 1714 Da (M+Na)$^+$, 1959 Da (M+Na)$^+$, 1975 Da (M+Na)$^+$ were observed. The peptide mixture obtained as shown in FIG. 3 was then taken up for possibility of peptaibol formation by MS/MS studies monitoring their diagnostic fragment ions.

Careful observation of mass spectra revealed the presence of diagnostic fragment ions with mass differences of m/z 85, characteristic for a peptaibol specific amino acid Aib in corresponding MS/MS spectra FIG. 3, cleavage of labile Aib-Pro motifs in molecule in CID conditions during MS/MS studies suggested that the peptide belonged to peptaibol class of peptides having many varied amino acid sequences. Peptides with m/z 1197, m/z 1213 and m/z 1976 were seen as major group whereas m/z 1415, m/z 1585, m/z 1714 were seen as minor group of peptaibols formation. Repeatability was observed at initial petri plate level for at least 5 times.

Example 3

Isolation of the Peptaibol from the Standard Liquid Condition of Endophytic Fungus *T. longibrachiatum* Having Accession No. MTCC 5721 and Confirmation of Peptaibol Formation Majorly from Cell Mass Screened endophytic strain of *Trichoderma longibraciatum* having accession no. MTCC 5721 as obtained in example 2 was taken further for upscaling for peptaibol production in shake flask condition and for further isolation. After 28 days of growth, 1.8 litres of *Trichoderma longibraciatum* having accession number MTCC 5721 culture was filtered to separate mycelia and spores from total culture growth. The cell mass was macerated with methanol for 2 hours. Wet mycelia was extracted 3 times with DCM:MeOH in the ratio of 1:1 and then 2:1 at room temperature of 28° C. Extracts were then combined and again re-extracted with ethyl acetate and evaporated to dryness under reduced pressure of 0.2-0.5 bars at 35° C. to give a crude peptaibol mixture (800 mg).

Figure 4:
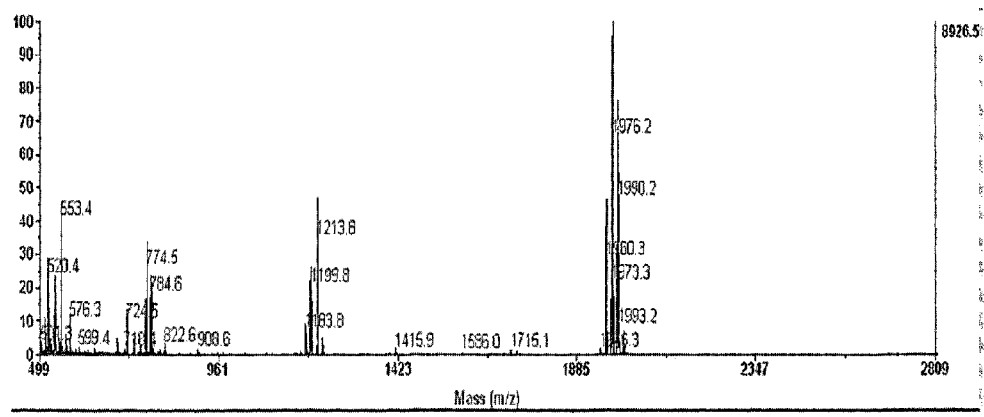
FIG. 4 provides the MS study from total growth, showing repeatability of ICMS results in shake flask conditions.

Mass spectra revealed a crude peptaibol mixture supporting the ICMS data. Mass studies by MALDI-TOF/TOF mass spectrometer of a small fraction of cell mass taken from the total growth provided mass of m/z 1199, m/z 1213, m/z 1415, m/z 1715 and m/z 1976 Da confirming the peptaibol formation in shake flask condition as well as. The mass studies obtained by MALDI-TOF/TOF mass spectrometer is provided in FIG. 4. Following masses were observed from the peptaibols taken from the shake flask condition which were same as observed for the peptaibols taken from static condition: m/z 1169 Da (M+Na)$^+$, 1183 Da (M+Na)$^+$, 1197 Da (M+Na)$^+$, 1199 Da (M+Na)$^+$, 1213 Da (M+Na)$^+$, 1415 Da (M+Na)$^+$, 1585 Da (M+Na)$^+$, 1714 Da (M+Na)$^+$, 1959 Da (M+Na)$^+$, 1975 Da (M+Na)$^+$.

Example 4

Figure 5:
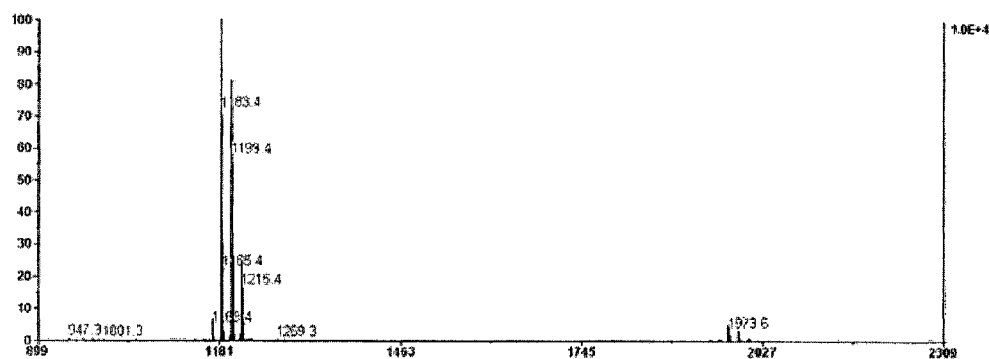
FIG. 5 (a) provides the Mass spectra showing separation of 11 mer chain of peptaibol from the rest mixture of peptaibols.
Figure 5:
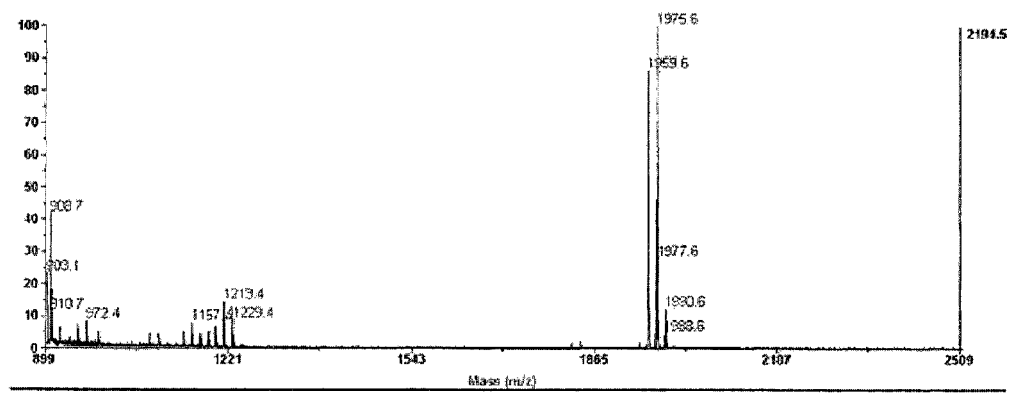

HPLC System for Separation of Peptaibol and their Biological Activity 800 mg of crude mixture as obtained from the process provided in example 3 was further purified by semi preparative HPLC with a Agilent 1200 series. Semi prep (Waters Spherisorb ODS 2, 5 µm, 250×10 mm) column was applied. Elution was carried out with binary mobile phase (ACN: H$_2$O) delivered at a constant flow rate of 2 ml/min. Volumes of 200 µl of 10 mg/ml sample solution in methanol were injected. Detection was performed at 214, 220, 254 nm. Gradient grade was set % B as ACN at rate of 40% at 0 min, till 5 min, then 95% till 45 min, continuing till 55% and at 60 min back to 40% ACN. Under the mentioned conditions indicated, medium 11 mer residual chain with m/z as 1183, 1197, 1199, 1213 had separated (FIG. 5). FIG. 5 (*a*) provides the Mass spectra showing separation of 11 mer chain of peptaibol from the rest mixture of peptaibols. FIG. 5 (*b*) provides the Mass spectra showing separation of long chain of peptaibols from the mixture of peptaibols. After concentrating in vacuum and freeze drying, fraction 4 (HF-4) was obtained, with amount of 38 mg at 30 minutes.

Example 5

Biological and Pharmacological Analysis

Figure 6:
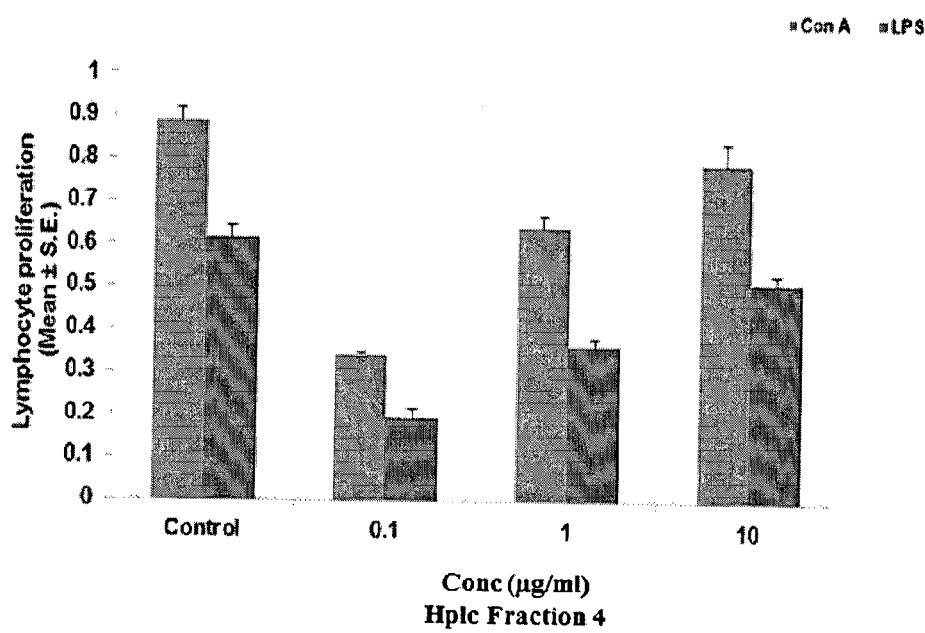
FIG. 6 shows the screening of purified extract HF-4 for immunomodulatory activity.

Fraction 4 (HF-4) obtained in accordance with example 4 was subjected to experiments to establish its pharmacological property against lymphocyte proliferation. It was found to be an immunosuppressant after the test as depicted in FIG. 6. FIG. 6 provides purified extracts with m/z 1183, 1199 with possible 11 mer chain length showing suppression of lymphocyte proliferation at concentration in range from 0.1 µM-10 µM in vitro. The extract was able to suppress the lymphocyte proliferation at a concentration as low as 0.1 µg/ml. Fraction 4 (HF-4) elicited significant decrease in (p<0.01) in proliferative response in the con-A stimulated lymphocytes. The increase in proliferation of cells was observed in dose dependent manner with IC$_{50}$ decrease in T and B-cell proliferation was observed at 0.1 µg/ml. Further doses 1-10 µg/ml revealed moderate decrease in cell proliferation.

Fraction 4 (HF-4) was also subjected to pharmacological analysis as an anticancer agents against various cell lines.

Cytotoxicity assay was performed on a panel of cancer cell lines using fraction 4 (HF-4) as a test material. In order to determine their effect on cell proliferation, A-549 (lung cell line), HEP-2 (liver cell line), MCF-7 (breast cell line), monkey normal cell line (CV-1), OVCAR-5 (ovary cell line) and THP-1 (leukemia cell line) were treated at indicated concentration of 50 µM for 48 h. These results obtained for fraction 4 (HF-4) showing the anti-cancer activity in general is provided in Table 2. As depicted in table, OVCAR-5, MCF-7 and THP-1 cancer cell lines were found to be highly sensitive to the HF-4 showing more than 95% growth inhibition at 50 µM concentration. However A-549 and HEP-2 showed slightly lesser sensitivity with upto 79% and 87% respectively. In addition CV-1, which is a normal monkey cell line were found to be least affected by HF-4. 5-flurouracil and adriyamycin were used as the positive controls; 5-flurouracil inhibited the growth of lung and leukemia cancer cell lines upto 75% and 83% respectively. Moreover adriyamycin used at 1 µM could inhibit the proliferation of MCF-7 cells upto 73%.

TABLE 2

| | | | Tissue Type | | | | |
| | | | Lung | Liver | Breast | Normal monkey Cell Line Type | Ovary | Leukemia |
| S. No. | Sample | Conc. (µM) | A-549 | HEP-2 | MCF-7 | CV-1 | OVCAR-5 | THP-1 |
| | | | | | % growth inhibition | | | |
| 1 | HF-4 (Peptaibol) (1199Da) | 50 | 79 | 87 | 99 | 2 | 93 | 99 |
| 2 | 5-Fluorouracil | 20 | 75 | — | — | — | — | 83 |
| 3 | Adriyamycin | 1 | — | — | 73 | — | — | — |

Example 6

Characterization of Brachiatin D Through MALDI TOF/TOF

Figure 7:
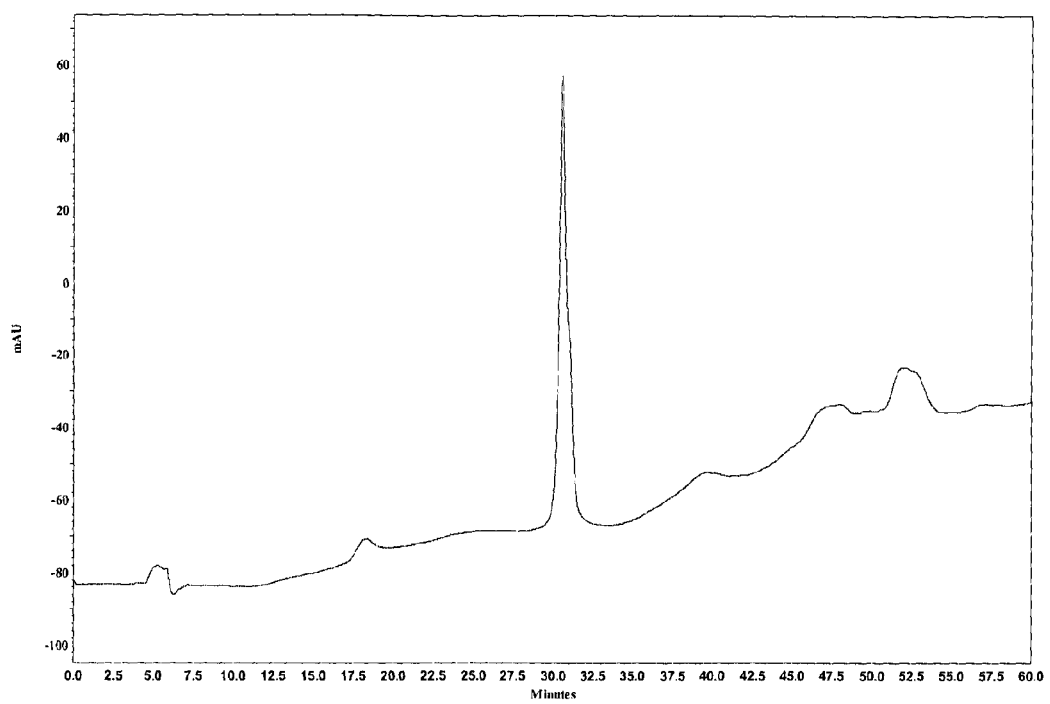
FIG. 7 shows the HPLC profile of purified Brachiatin D.

Fraction 4 (HF-4) was further purified on Agilent series with Waters Spherisorb ODS 2, 5 µm, 250×10 mm with eluent as 0.1% trifluroacetic acid in a linear gradient 75% ACN at a flow rate of 1 ml/min with UV absorption at 220 and 254 nm to give 8.2 mg of a peptaibol named Brachiatin D as characterized by MALDI TOF/TOF having the sequence as AcAib-Asn-Aib-Leu-Aib-Pro-Aib-Asn-Leu-Pro-Ileuol (FIG. 7). FIG. 7 shows the HPLC profile of purified Brachiatin D.

Figure 8:
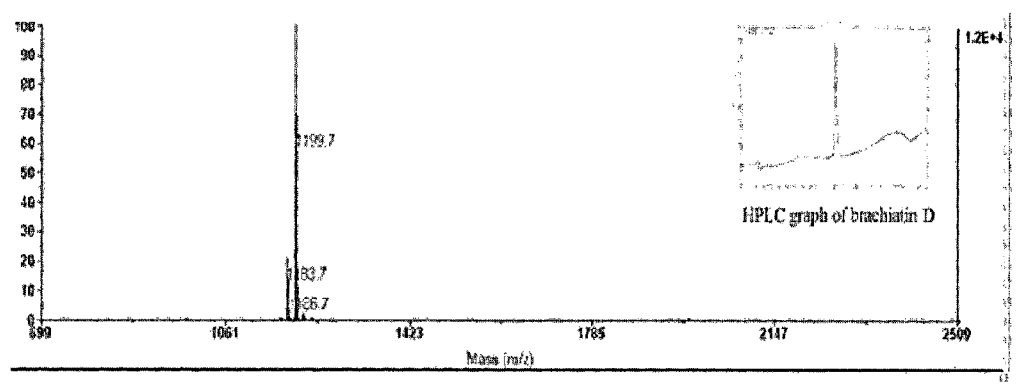
FIG. 8 (a) provides the Mass spectra of the purified Brachiatin. D isolated from *Trichoderma longibrachiatum* having MTCC number 5721.
Figure 8:
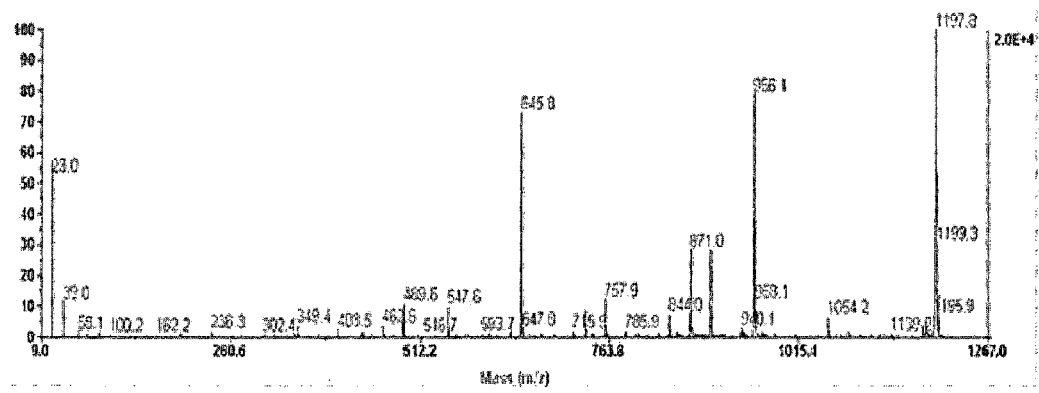
Figure 9A:
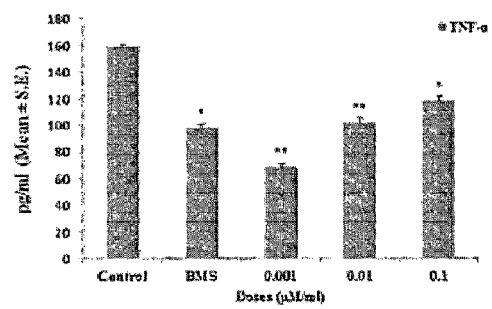
FIG. 9 (a) shows the effect of purified Brachiatin D on the level of TNF-α.
Figure 9B:
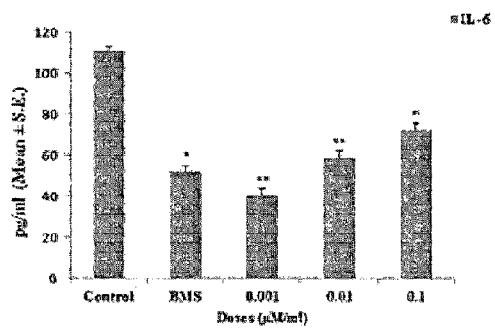
Figure 9C:
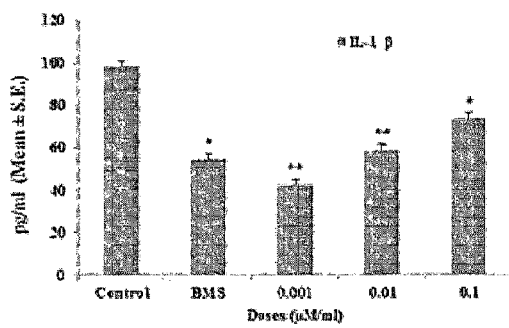
Figure 9D:
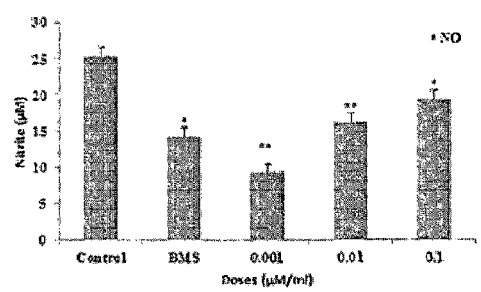

Assignment of brachiatin D done through fragmentation studies by Tof/Tof in high collision energy and high voltage of 2 KV giving sequence with presence of a, b and immonium ions with m/z 58, 70, 86, 87, 128, 349, 462, 547, 645, 730, 843, 955, 1053 Da (FIG. 8). FIG. 8 (a) provides the Mass spectra of the purified Brachiatin D isolated from *Trichoderma longibrachiatum* having MTCC number 5721. FIG. 8 (b) provides the MS/MS studies of purified Brachiatin D having mass with m/z 1199 Da.

Example 7

Biological Activity of Brachiatin D on Cytokine Production

For estimation of pro-inflammatory cytokines (TNF-α, IL-1β and IL-6) in spleen cell culture supernatant, the splenocytes ($2 \times 10^6$ cells) were seeded into a 96-well flat-bottom microtiter plate in 100 μl complete medium. Thereafter, variable does of purified brachiatin D (0.001, 0.01 and 0.1 μM) were added giving a final volume of 200 μl. After subsequent stimulation with 1 μg/ml LPS for 24 h, the supernatants were harvested. The concentrations of TNF-α, IL-1β and IL-6 in culture supernatants were measured using mouse TNF-α, IL-1β and IL-6 ELISA kits (R&D Systems, USA), as per the instructions of the manufacturer.

Brachiatin D inhibited LPS induced macrophages activation (Pro-iflammatory Cytokines: TNF-α, IL-1 βeta and IL-6). Model of LPS stimulated cell systems have been adopted for activity determination of the test molecule. Mouse macrophages were used with cells stimulated with LPS (1 μg/ml) along with different dose range i.e. 0.001-0.1 μg/ml of brachiatin. D. Cell culture media collected at 24 h were assayed for Pro inflammatory cytokines IL-1 β, IL-6 and TNF-α by using commercial ELISA Kits (R&D Quantikine). It was decided to determine TNF-α at 24 h, as previous study showed LPS could stimulate cells to produce large quantity of TNF-α in culture media as early as 6 h. The result obtained is provided in FIG. 9. FIG. 9 (a) shows the effect of purified Brachiatin D on the level of TNF-α. FIG. 9 (b) shows the effect of purified Brachiatin D on the level of IL-6. FIG. 9 (c) shows the effect of purified Brachiatin D on the level of IL-1 β.

It was observed that brachiatin D could inhibit TNF-α production dose dependently up to 42%. Further, in addition to TNF-α, it was further studied whether brachiatin D could regulate the expression of IL-6 and IL-1β production.

Inhibition of Nitric Oxide (NO) by Brachiatin D

NO is a short-lived molecule. Therefore, more stable product, nitrite was measured in the cell culture media of cells treated with LPS. Large quantity of nitrite is produced by macrophage when stimulated with LPS. But when cells were treated with brachiatin D, it was observed that brachiatin D inhibited LPS stimulated production of nitrite (p<0.001 at 0.001 μM dose). FIG. 9 (d) shows the effect of purified Brachiatin D on the level of NO. Marginal increase in NO production was observed at 0.1 μM concentration p<0.05 (FIG. 9). The purified brachiatin D obtained showed good activity against proinflammatory cytokines TNF alpha, IL-1 β, IL-6, NO and lymphocyte proliferation at concentration range from 0.001 μM-10 μM as shown in FIG. 9.

Determination of Anticancer Activity

The purified brachiatin D obtained showed promising activity against various cell lines. Cytotoxicity assay based on MTT was performed on a panel of cancer cell lines using brachiatin D as a test material. The purified brachiatin D showed differential cytotoxicity against various cell lines as A-549 (lung cell line), HOP-62 (lung cell line), THP-1 (leukemia cell line), PC-3 (Prostate cell line), MCF-7 (Breast cell line), MiaPaCa-2 (Pancreatic cell line) and having optimal growth inhibition >56% to 100% in human cell lines at 10 μM as shown in Table 3. Among the two lung cancer cell lines, brachiatin D showed specificity towards A-549 cell line showing >95% inhibition at 20 μM concentration which decreased to lesser extent upto 63% at 10 μM concentration. HOP-62 which is again a lung cancer cell line showed much resistance towards brachiatin D. In addition, MCF-7, MiaPaCa-2 and PC-3 were found to be highly sensitive to the cytotoxic effects of brachiatin D showing 100% inhibition even at 10 μM concentration. Again THP-1 were also found to sensitive to brachiatin D showing >75% inhibition at 20 μM concentration. 5-flurouracil and adriyamycin were used as the positive controls; 5-flurouracil inhibited the growth of lung and leukemia cancer cell lines upto 73%, 81% and 88% respectively. Adriyamycin used at 1 μM could inhibit the proliferation of MCF-7 cells upto 77%.

TABLE 3

| | | Tissue Type | | | | | |
|---|---|---|---|---|---|---|---|
| | | Lung | Lung | Breast | Pancreatic | Prostate | Leukemia |
| | | | | Cell Line Type | | | |
| | | A-549 | HOP-62 | MCF-7 | MiaPaCa-2 | PC-3 | THP-1 |
| Conc. (μM) | | | | % age growth inhibition | | | |
| 20 | Brachiatin D | 96 | 35 | 100 | 100 | 100 | 77 |
| 10 | | 63 | 21 | 100 | 100 | 100 | 56 |
| 20 | 5-Fluorouracil | 73 | 81 | — | — | — | 88 |
| 01 | Adriyamycin | — | — | 77 | — | — | — |

Advantages of the Invention

1. Brachiatin D having sequence as set forth as AcAib-Asn-Aib-Leu-Aib-Pro-Aib-Asn-Leu-Pro-Ileuol has potent activity against proinflammtory cytokines like TNF-α, IL-1β, IL-6, NO and lymphocyte proliferation in range of 0.001 μM-10 μM.

2. The peptaibol has potent activity against various cancer cell lines such as A459 (lung cell line), HOP-62 (lung cell line), THP (leukemia cell line), PC-3 (Prostrate cell line), MCF-7 (Breast cell line) and MiaPaca-2 (Pancreatic cell line) with $IC_{50}$ in range of 1 μM-7 μM.

We claim:
1. A composition comprising an isolated peptaibol having sequence AcAib-Asn-Aib-Leu-Aib-Pro-Aib-Asn-Leu-Pro-Ileuol, a pharmaceutically acceptable carrier or a diluent, and a preservative and/or stabilizer, wherein AcAib is acetylated α aminoisobutyric acid, Aib is α aminoisobutyric acid, Asn is Asparagine, Leu is Leucine, Pro is Proline and Ileuol is Isoleucinol,
represented by structure I,

Structure I

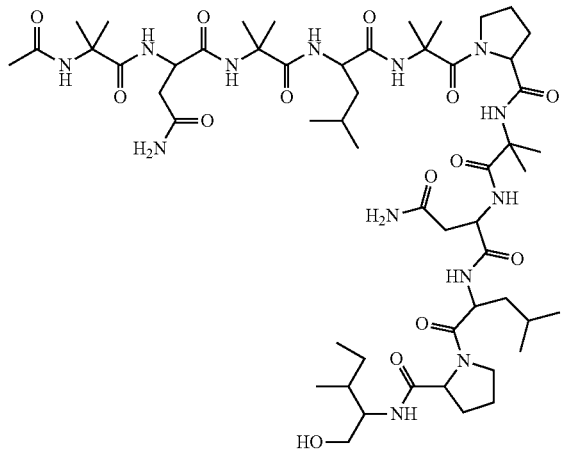

Ac-Aib-Asn-Aib-Leu-Aib-Pro-Aib-Asn-Leu-Pro-Ileol said peptaibol having optimal growth inhibition in the range of >56%-100% in human cancer cell lines at a concentration ranging between 1 μM-50 μM and having $IC_{50}$ values in the range of 1 μM-7 μM against cancer cell lines selected from the group consisting of A549 (lung cell line), HOP-62 (lung cell line), THP1 (leukemia cell line), PC-3 (Prostrate cell line), MCF-7 (Breast cell line) and MiaPaCa-2 (Pancreatic cell line).

2. The composition of claim 1, wherein said peptaibol exhibits activity against proinflammatory cytokines TNF α, IL-1β, IL-6, activity against NO, and activity against lymphocyte proliferation at a concentration in the range of 0.001 μM-10 μM.

3. A process for obtaining the peptaibol comprised in the composition of claim 1, the process comprising the following steps:
(a) isolating an endophytic fungus *Trichoderma longibrachiatum*;
(b) obtaining a suspension of conidia of the fungus by growing the fungus obtained in step (a) in a media;
(c) inoculating a flask containing a broth with the suspension containing $10^5$ to $10^6$ conidia/ml of the fungus and incubating at a temperature in the range of 22 to 28° C. under shaking conditions at 130-200 rpm for 15 to 30 days to obtain a broth of fungal mycelia;
(d) separating the fungal mycelia and conidia from the broth and macerating the fungal mycelia with a solvent for a time period of 45 min to 2 hours to obtain an extract;

(e) evaporating the extract to dryness under reduced pressure in the range of 0.2 to 0.5 bar at a temperature in the range of 25 to 40° C. to obtain a crude mixture; and
(f) purifying the crude mixture obtained in step (e) by chromatography to obtain the peptaibol.

4. The process as claimed in claim 3 wherein the media used in step (b) is selected from the group consisting of Malt Extract Broth Base and Potato Dextrose Broth.

5. The process as claimed in claim 3, wherein the *Trichoderma longibrachiatum* is isolated from *Boswellia serrata*.

6. The process as claimed in claim 3, wherein the broth used is selected from the group consisting of Malt Extract Broth or Potato Dextrose Broth.

7. The process as claimed in claim 3, wherein the solvent used is selected from the group consisting of methanol, dichloromethane and ethyl acetate or a mixture thereof.

8. The process as claimed in claim 3, wherein the yield of peptaibol is in the range of 30 mg to 80 mg from 100 to 900 mg of crude mixture.

9. The process as claimed in claim 3, wherein the peptaibol obtained is 99% pure.

10. The process as claimed in claim 3, wherein the chromatography used is HPLC or reverse phase chromatography.

11. The process as claimed in claim 10, wherein the reverse phase chromatography is carried out using hydrophobic material RP-8 or RP-18 with a solvent system selected from the group consisting of acetonitrile and trifluoro acetic acid or a mixture thereof.

12. A composition comprising an isolated fungal strain of *Trichoderma longibrachiatum* having accession number MTCC 5721, wherein the fungus is lyophilized conducive to long term storage and/or wherein the composition further comprises a growth medium selected from one or more of potato dextrose broth, potato dextrose agar, malt extract broth, malt extract agar, yeast malt broth, and yeast malt agar.

13. The composition of claim 1, for use in inhibition of cytokines selected from the group consisting of TNF α, IL-1β and IL-6 and in treatment of cancer selected from the group consisting of lung, leukemia, prostate, pancreatic, and/or breast cancer.

14. The composition of claim 1, wherein the composition is formulated in a capsule and/or as a tablet wherein composition is enveloped by a polymeric material.

15. The composition of claim 12, wherein the fungus is lyophilized conducive to long term storage.

16. A method of inhibiting TNF α, IL-1β, and/or IL-6 in a subject in need thereof, comprising administering the composition of claim 1 to the subject.

17. A method of inhibiting NO in a subject in need thereof, comprising administering a therapeutically effective amount of the composition of claim 1 to the subject.

18. A method of treating lung, leukemia, prostate, pancreatic, and/or breast cancer in a subject in need thereof, comprising administering a therapeutically effective amount of the composition of claim 1 to the subject.

* * * * *

SEQUENCE LISTING

```
<160> NUMBER OF SEQ ID NOS: 4

<210> SEQ ID NO 1
<211> LENGTH: 11
<212> TYPE: PRT
<213> ORGANISM: Trichoderma longibrachiatum
<220> FEATURE:
<221> NAME/KEY: MOD_RES
<222> LOCATION: (1)..(1)
<223> OTHER INFORMATION: AcAib
<220> FEATURE:
<221> NAME/KEY: MOD_RES
<222> LOCATION: (3)..(3)
<223> OTHER INFORMATION: Aib
<220> FEATURE:
<221> NAME/KEY: MOD_RES
<222> LOCATION: (5)..(5)
<223> OTHER INFORMATION: Aib
<220> FEATURE:
<221> NAME/KEY: MOD_RES
<222> LOCATION: (7)..(7)
<223> OTHER INFORMATION: Aib
<220> FEATURE:
<221> NAME/KEY: MOD_RES
<222> LOCATION: (11)..(11)
<223> OTHER INFORMATION: Ile-ol

<400> SEQUENCE: 1

Xaa Asn Xaa Leu Xaa Pro Xaa Asn Leu Pro Xaa
1               5                   10

<210> SEQ ID NO 2
<211> LENGTH: 19
<212> TYPE: DNA
<213> ORGANISM: Artificial sequence
<220> FEATURE:
<223> OTHER INFORMATION: ITS1, Forward primer sequence

<400> SEQUENCE: 2
tccgtaggtg aacctgcgg                                             19

<210> SEQ ID NO 3
<211> LENGTH: 20
<212> TYPE: DNA
<213> ORGANISM: Artificial sequence
<220> FEATURE:
<223> OTHER INFORMATION: ITS4, Reverse primer sequence

<400> SEQUENCE: 3
tcctccgctt attgatatgc                                            20

<210> SEQ ID NO 4
<211> LENGTH: 22
<212> TYPE: DNA
<213> ORGANISM: Artificial sequence
<220> FEATURE:
<223> OTHER INFORMATION: ITS5, Forward primer sequence

<400> SEQUENCE: 4
ggaagtaaaa gtcgtaacaa gg                                         22
```